United States Patent [19]
Suggs et al.

[11] Patent Number: 5,527,864
[45] Date of Patent: Jun. 18, 1996

[54] POLY(PROPYLENE FUMARATE-CO-ETHYLENE OXIDE)

[76] Inventors: Laura J. Suggs; Richard G. Payne, both of Rice University, 6100 Main St,, Houston, Tex. 77005; Michael J. Yaszemski, Lackland A.F.B., 59th Medical Wing/PSSB, 2200 Bergquist Dr., Ste. #1, San Antonio, Tex. 78236; Antonios G. Mikos, Rice University, 6100 Main St., Houston, Tex. 77005

[21] Appl. No.: 512,308
[22] Filed: Aug. 8, 1995
[51] Int. Cl.⁶ .................................................. C08F 20/00
[52] U.S. Cl. .......................... 525/444; 525/437; 524/717; 424/421; 424/422; 623/11
[58] Field of Search ...................... 525/437, 444; 524/717; 424/421, 422; 623/11

[56] References Cited

U.S. PATENT DOCUMENTS 4,888,413  12/1989  Domb ..................................... 528/272
5,213,580   5/1993  Slepian et al. .............................. 623/1

OTHER PUBLICATIONS

A. J. Domb et al., "The Formation of Propylene Fumarate Oligomers for Use in Bioerodible Bone Cement Composites," *Journal of Polymer Science: Part A: Polymer Chemistry*, vol. 28 (1990), pp. 973–985.

J. M. Harris, "Introduction to Biotechnical and Biomedical Applications of Poly(Ethylene Glycol)," *Poly(Ethylene Glycol) Chemistry: Biotechnical and Biomedical Applications*, 1992, pp. 1–3.

A. S. Sawhney et al., "Bioerodible Hydrogels Based on Photopolymerized Poly(ethylene glycol(–co–poly(α–hydroxy acid) Diacrylate Macromers," *Macromolecules*, 1993, 26, pp. 581–587.

*Primary Examiner*—Samuel A. Acquah
*Attorney, Agent, or Firm*—Pravel, Hewitt, Kimball & Krieger

[57] ABSTRACT

A biodegradable block copolymer made from the transesterfication of a poly(propylene fumarate) prepolymer and a poly(ethylene oxide) prepolymer. The block copolymer poly(propylene fumarate -co- ethylene oxide) is capable of crosslinking at body temperature. Crosslinking requires an appropriate crosslinking monomer and an initiator. The biodegradable block copolymer has utility as a vascular implant because it can be injected as a fluid into the vascular system and crosslinked in situ.

7 Claims, 2 Drawing Sheets

POLY(PROPYLENE FUMARATE-CO-ETHYLENE OXIDE)

BACKGROUND

1. Field of the Invention

This invention relates to a block copolymer identified as poly(propylene fumarate -co- ethylene oxide), to a method of synthesizing this block copolymer and to a method of using it.

2. Description of the Prior Art

Polymers have found significant utility in the modern world. Whenever there is a particular need for a material having a specific property or set of properties, scientists often look to polymers to meet that need. In the field of medicine, for example, there is a continuing need for polymers that meet very specific requirements. Some of the properties of a polymer that may be important in biomedical applications, include biocompatability, mechanical strength, consistency, plasticity, resiliency, permeability, crosslinking ability and biodegradability.

One polymer that has been successfully used in the field of medicine is poly(propylene fumarate) (PPF). U.S. Pat. No. 4,888,413, issued to Domb, describes some of the medical uses for PPF and various methods of synthesizing it. Also, PPF has been described in Biopolymeric Controlled Release Systems Volume II, Donald L. Wise, et al., Chapter 11, 170–184, and in "The Formation of Propylene Fumarate" Oligomers for Use in Bioerodible Bone Cement Composites," by A. J. Domb, et al., Journal of Polymer Science: Part A: Polymer Chemistry, Vol 28, 973–985 (1990). Generally, poly(propylene fumarate) is useful as a bone cement because it crosslinks to form a solid having appropriate compressive strength.

Another polymer that has been used in other applications in the medical field is poly(ethylene oxide) (PEO) which has the chemical composition, $HO\text{-}[\text{-}CH_2\text{-}CH_2\text{-}O\text{-}]_m\text{-}H$. This compound is also called poly(ethylene glycol) (PEG) when the molecular weight is less than about 20,000. In this description, the term "PEO" will be used generally to describe the chemical composition, $HO\text{-}[\text{-}CH_2\text{-}CH_2\text{-}O\text{-}]_m\text{-}H$, without regard to the molecular weight. Some of the medical applications of PEO are discussed in Poly(Ethylene Glycol) Chemistry: Biotechnical and Biomedical Applications, edited by J. M. Harris, 1992.

PEO has also been used in the medical field as a copolymer. For example, "Bioerodible Hydrogels Based on Photopolymerized Poly(ethylene glycol)-co-poly($\alpha$-hydroxy acid) Diacrylate Macromers," Macromolecules, A. S. Sawhney, et al., vol 26, 581–587, describes a copolymer that functions as a biodegradable hydrogel for delivering drugs.

However, these polymers and copolymers are not suitable in some specialized applications. For example, it would be desirable to have a biodegradable polymer that is crosslinkable at body temperature, i.e., about 37° C. Such a polymer would have special utility as a material for vascular implants. Instead of inserting a solid vascular implant which has the potential of damaging the walls of an artery during implantation, the surgeon could simply inject through a catheter a fluid polymer which could be crosslinked in situ to form a vascular implant. Such a material would permit the implantation of a vascular implant without unduly traumatizing the walls of the artery.

SUMMARY OF THE INVENTION

The present invention comprises a block copolymer developed from prepolymers poly(propylene fumarate) and poly(ethylene oxide). An important characteristic of the block copolymer poly(propylene fumarate -co- ethylene oxide) is that it crosslinks in a few minutes at approximately body temperature, i.e., at about 37° C., and it is biodegradable. Therefore, it can be inserted into the body in fluid form and crosslinked in situ to form a biodegradable implant. The crosslinking step requires an appropriate crosslinking monomer along with a radical initiator. An accelerator may also be used to increase the rate of crosslinking.

DESCRIPTION OF THE PREFERRED EMBODIMENT

It has been discovered that a biodegradable block copolymer poly(propylene fumarate -co- ethylene oxide) can be made from the transesterfication of a poly(propylene fumarate) prepolymer and a poly(ethylene oxide) prepolymer and that this block copolymer can be crosslinked by addition polymerization with a suitable crosslinking monomer. The crosslinking process requires a radical initiator, and it occurs at approximately body temperature, i.e., about 37° C., so it is ideally suited for medical use as a biodegradable implant. An accelerator may also be used to speed the rate of crosslinking.

Figure 1:
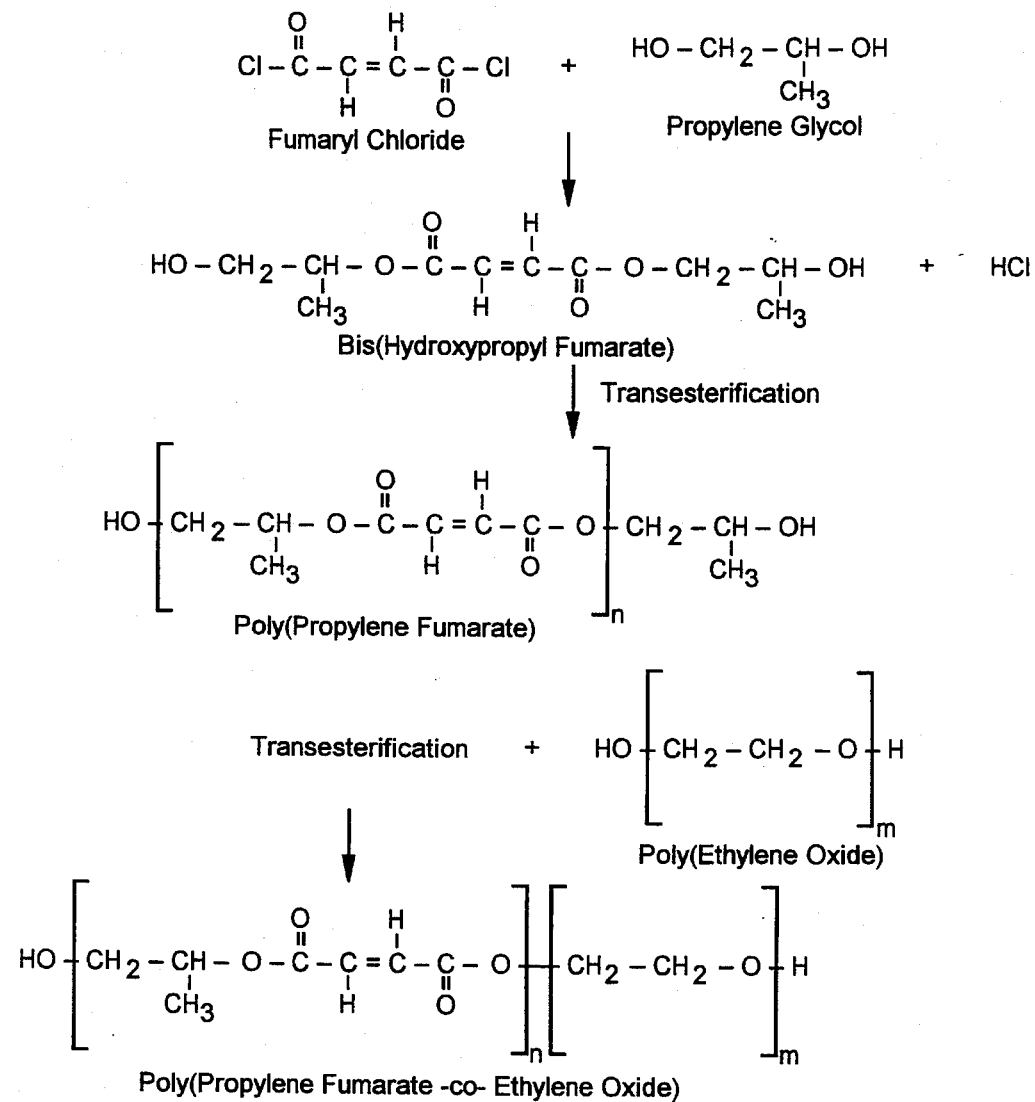
FIG. 1 shows a reaction pathway for producing block copolymer poly(propylene fumarate -co- ethylene oxide).

Referring to FIG. 1, the starting monomer, bis(hydroxypropyl fumarate) is made by the exothermic reaction of fumaryl chloride and propylene glycol. The prepolymer poly(propylene fumarate) is produced by a condensation reaction of the starting monomer, and preferably it has a repeating unit "n", such that the molecular weight of the prepolymer ranges from about 300 to about 12,000.

The prepolymer poly(propylene fumarate) can be made by any acceptable method. However, the preferred method for producing poly(propylene fumarate) is described in Example 1. A more complete description of this synthesis process is contained in pending United States patent application Ser. No. 08/234,551 filed Apr. 28, 1994, which is incorporated herein by reference.

EXAMPLE 1

Fumaryl chloride is added slowly to a three times excess of propylene glycol at ambient temperature in the absence of any catalyst. Hydrochloric acid is given off as a gas in this exothermic reaction, and the trimer, bis(hydroxypropyl fumarate) is formed. This trimer is purified in a solution precipitation by dissolving it in tetrahydrafuran (THF) and precipitating it in a six fold volume of petroleum ether. The second step is the transesterification of the trimer at approximately 160° C. under a vacuum of 100 mm Hg. Antimony trioxide is added as a basic catalyst, and propylene glycol is removed by condensation.

The prepolymer poly(ethylene oxide), is a polymer that can be made by a variety of methods known to those skilled in the art, and it has repeating units "m", such that the molecular weight of the prepolymer ranges from about 50 to about 20,000. As mentioned earlier, it is also known as poly(ethylene glycol) (PEG) but will be referred to herein as poly(ethylene oxide) (PEO).

In the preferred embodiment of this invention, the block copolymer is formed by adding poly(ethylene oxide) which is incorporated by further condensation of its terminal hydroxyl groups with the poly(propylene fumarate) oligomers under the same conditions used to form the prepolymer poly(proplyene fumarate). Poly(ethylene oxide) is reacted with poly(propylene fumarate) at approximately 160° C. under a vacuum of 100 mm Hg, and antimony trioxide is added as a basic catalyst. The block copolymer is purified in a solution precipitation by dissolving it in THF and precipitating it in a six fold volume of petroleum ether.

The chemical reaction between PEO and PPF occurs when the terminal hydroxyl group on PEO attacks a carbonyl site on PPF, either internally or terminally. It should be noted that if an internal carbonyl site on PPF is involved, the block of PPF that attaches to PEO to form the block copolymer of this invention will have a lower molecular weight than the starting PPF prepolymer because the starting PPF prepolymer will be cleaved at that carbonyl site. Therefore, it is probable that the copolymerization step will lower the molecular weight of the PPF prepolymer as it reacts with PEO.

The resulting block copolymer can be crosslinked by addition polymerization using an appropriate crosslinking monomer along with a radical initiator. Preferably, an accelerator will also be added to speed the rate of crosslinking. Suitable crosslinking monomers include, methylmethacrylate, N-vinylpyrrilidone and hydroxyethylmethacrylate. Suitable radical initiators are benzoyl peroxide, azobisisobutyronitrile, or acetyl peroxide, and a suitable accelerator is N,N-dimethyltoluidine. This crosslinking reaction takes place within a matter of minutes at body temperature, i.e., about 37° C. Calorimetric studies have shown that the crosslinking temperature rises less than 10° C. when starting from 25° C.

The molecular weight of the block copolymer poly(propylene fumarate -co- ethylene oxide) depends primarily on the molecular weight of the poly(propylene fumarate) and poly(ethylene oxide) starting prepolymers. The poly(propylene fumarate) component provides the rigidity characteristic for the copolymer and allows the copolymer to be crosslinked at body temperatures. The poly(ethylene oxide) component gives the copolymer its mechanical compliance, i.e., it provides flexibility. The molecular weight of each prepolymer and the ratio of the prepolymer components will affect the physical properties of the resulting block copolymer. For example, a higher ratio of poly(propylene fumarate) will yield a more rigid block copolymer when crosslinked, while a higher ratio of poly(ethylene oxide) will yield a more pliable crosslinked block copolymer. Therefore, the physical characteristics of the crosslinked block copolymer can be tailored to fit its end use.

Several block copolymers were prepared to determine the effect, if any, that varying the parameters had on the properties of the resulting block copolymers. This procedure was accomplished through the use of a resolution IV, two level fractional factoffal design, as described in an article entitled, "The Ingrowth of New Bone Tissue and Initial Mechanical Properties of a Degrading Polymeric Composite Scaffold," M. J. Yaszemski, et. al, *Tissue Eng.*, vol 1, pp 41–51. The design is given in Table I.

TABLE I

| | | Resolution IV fractional factorial design | | |
|---|---|---|---|---|
| Run Number | MW of PEO | PPF Reaction Time | Copolymer Reaction Time | PEO/PPF Ratio |
| 1 | 2,000 | 3 hours | 3 hours | 0.66 |
| 2 | 2,000 | 3 hours | 6 hours | 0.33 |
| 3 | 2,000 | 6 hours | 3 hours | 0.33 |
| 4 | 2,000 | 6 hours | 6 hours | 0.66 |
| 5 | 8,000 | 3 hours | 3 hours | 0.33 |
| 6 | 8,000 | 3 hours | 6 hours | 0.66 |
| 7 | 8,000 | 6 hours | 3 hours | 0.66 |
| 8 | 8,000 | 6 hours | 6 hours | 0.33 |

Figure 2:
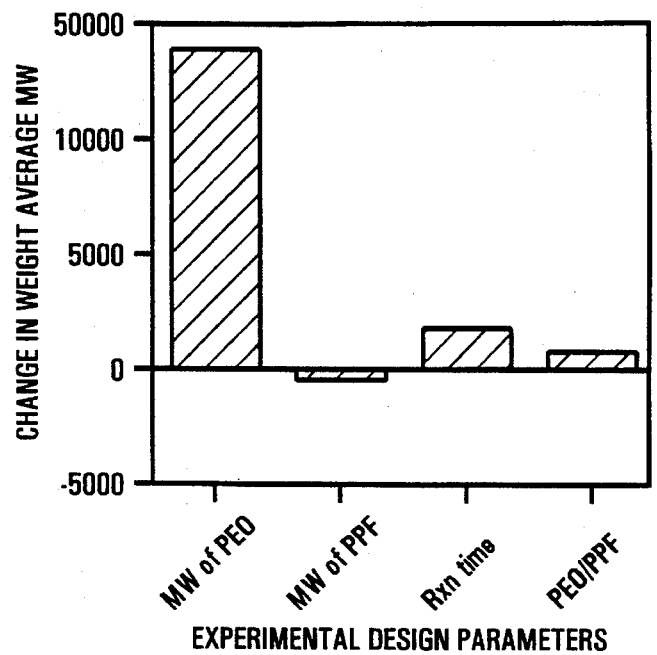
FIG. 2 is a graphic representation of parameters affecting molecular weight of the block copolymer.
Figure 3:
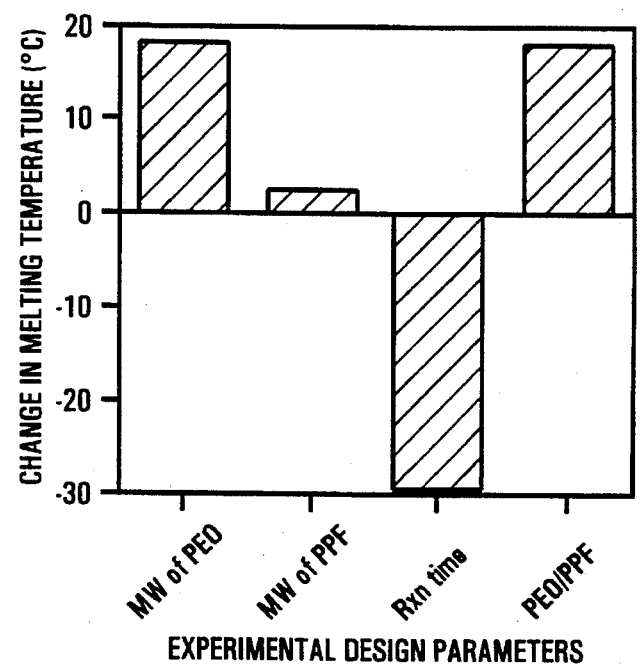
FIG. 3 is a graphic representation of parameters affecting melting temperatures of the block copolymer.

Table II shows the gel permeation chromatography (GPC) and differential scanning calorimetry (DSC) values obtained for the starting materials as well as the eight formulations of the copolymer. Some of this material is presented graphically in FIGS. 2 and 3. FIG. 2 shows that the molecular weight of the copolymer depends primarily on the molecular weight of the PEO starting material, while the other variables have little effect. In FIG. 3, it is evident that the molecular weight of the PEO and the ratio of PEO to PPF have a similar increasing effect on the melting temperature, while the reaction time of the copolymer has a strong reducing effect.

TABLE II

| | GPC and DSC data | | | | | |
|---|---|---|---|---|---|---|
| | $M_w$ | $M_n$ | $T_m$ onset | $T_m$ | $\Delta H_{fus}$ | $X_c$ |
| PPF (3 hrs) | 1610 | 1490 | — | — | — | — |
| PPF (6 hrs) | 1730 | 1560 | — | — | — | — |
| PEO 2,000 | 4240 | 4030 | 45.4 | 53.5 | 38.7 | — |
| PEO 8,000 | 18280 | 16690 | 54.6 | 61.4 | 36.0 | — |
| 1 | 7500 | 6020 | −5.7 | 26.7 | 12.2 | 37.7 |
| 2 | 8700 | 6890 | −7.5 | 23.7 | 8.5 | 52.6 |
| 3 | 6040 | 5370 | −7.7 | 35.0 | 9.2 | 56.9 |
| 4 | 9060 | 6920 | −13.6 | 25.9 | 12.8 | 39.6 |
| 5 | 21610 | 18840 | 6.2 | 44.6 | 11.4 | 70.5 |
| 6 | 23600 | 21000 | 22.4 | 48.2 | 23.9 | 73.9 |
| 7 | 22100 | 19270 | 28.8 | 55.6 | 21.9 | 67.7 |
| 8 | 22970 | 19570 | 3.8 | 35.1 | 13.8 | 85.3 |

$M_w$ = weight average molecular weight
$M_n$ = number average molecular weight
$T_m$ = melting temperature (°C.)
$\Delta H_{fus}$ = heat of fusion (cal/g)
$X_c$ = percent crystallinity The GPC chromatograms demonstrated the presence of unreacted PPF oligomers in the copolymer product. In addition, most of the copolymers showed a bimodal molecular weight distribution. DSC studies indicate the absence of any PEO homopolymer. The DSC thermograms show an increase in melting temperature with increasing crystallinity brought about by either increasing the molecular weight or the weight percent of PEO block. All the copolymer melting temperatures remain below that of the pure crystalline PEO due to the amorphous nature of PPF. The sharp decrease in melting temperature is also due to the increasing length of the amorphous chains. One skilled in the art would be able to design the appropriate block copolymer with the desired physical properties, depending upon its intended end use.

One end use of the block copolymer of this invention is as a biodegradable vascular implant. This block copolymer solves an important problem associated with vascular implants. Typically, an implant is a rigid tube designed to allow the flow of blood and other fluids through a vessel which otherwise would be restricted in some way. Inserting such a tube causes damage to the surrounding tissue which can lead to restenosis or excessive scarring of the tissue. The advantage of using the block copolymer poly(propylene fumarate -co- ethylene oxide) as a vascular implant is its ability to crosslink in situ which means that a fluid block copolymer can be inserted into an artery through a catheter and be polymerized inside the artery to form the implant. The degradation of this block copolymer will produce products that the body can metabolize and/or excrete.

Figure 4:
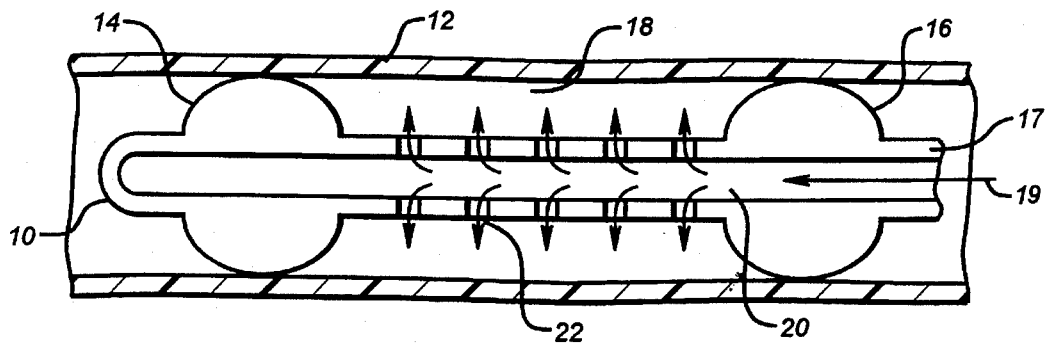
FIG. 4 is a cross-sectional view of an artery and catheter illustrating a method of implanting the block copolymer.

As illustrated in FIG. 4, the vascular implant can be formed in situ by using a double balloon perfusion catheter 10 to deliver the block copolymer of this invention. The catheter 10 is inserted into the artery 12 to the desired location. Balloons 14 and 16 attached to the distal end of the perfusion catheter 10 are inflated through peripheral channel 17 to isolate the space 18 between the balloons. Next, a fluid mixture 19 of the block copolymer, crosslinking monomer and initiator is injected through an annulus 20 in the catheter and exits the catheter through perforations 22 located between the inflated balloons. The mixture contacts the interior of the arterial wall 12, and it crosslinks within a few minutes by itself without the aid of any external means (such as light) to form the implant. The balloons 14 and 16 are deflated so the catheter 10 can be removed. The resulting implant will be held in place by tension from the arterial wall and will maintain an opening for the passage of blood. As the implant degrades, its constituents will be excreted from or absorbed by the body.

Having described the invention above, various modifications of the techniques, procedures, material and equipment will be apparent to those in the art. It is intended that all such variations within the scope and spirit of the appended claims be embraced thereby.

What we claim is:

1. A block copolymer comprising poly(propylene fumarate -co- ethylene oxide).

2. The block copolymer of claim 1 wherein the block copolymer is crosslinked.

3. The block copolymer of claim 2 wherein crosslinking will occur at a temperature of about 37° C.

4. The block copolymer of claim 1 wherein the copolymer has been crosslinked by addition polymerization at a temperature of about 37° C.

5. The block copolymer of claim 1 wherein the weight average molecular weight of the prepolymer poly(propylene fumarate) ranges from about 300 to about 12,000.

6. The block copolymer of claim 1 wherein the weight average molecular weight of the prepolymer poly(ethylene oxide) ranges from about 50 to about 20,000.

7. The block copolymer of claim 1 wherein the weight average molecular weight of the prepolymer poly(propylene fumarate) ranges from about 300 to about 12,000 and the molecular weight of the prepolymer poly(ethylene oxide) ranges from about 50 to about 20,000.

* * * * *